(12) United States Patent
Havens et al.

(10) Patent No.: US 6,306,348 B1
(45) Date of Patent: *Oct. 23, 2001

(54) INORGANIC PERMEATION LAYER FOR MICRO-ELECTRIC DEVICE

(75) Inventors: John R. Havens; Michael K. Krihak, both of San Diego; Charles H. Greef, Ramona; Daniel E. Raymond, San Diego; Michael J. Heller, Encinitas, all of CA (US)

(73) Assignee: Nanogen, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/354,931

(22) Filed: Jul. 15, 1999

Related U.S. Application Data

(63) Continuation-in-part of application No. 08/986,065, filed on Dec. 5, 1997, now Pat. No. 6,051,380, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662, application No. 09/354,931, which is a continuation-in-part of application No. 08/708,262, filed on Sep. 6, 1996.

(51) Int. Cl.$^7$ .............................. G01N 15/00; G01N 1/00; C12Q 1/68
(52) U.S. Cl. ................................. 422/68.1; 422/50; 435/6
(58) Field of Search ........................ 422/50, 68.1; 435/6

(56) References Cited

U.S. PATENT DOCUMENTS

| | | | |
|---|---|---|---|
| 5,605,662 | 2/1997 | Heller et al. | 422/68.1 |
| 5,632,957 | * 5/1997 | Heller et al. | 422/68.1 |
| 5,849,486 | * 12/1998 | Heller et al. | 435/6 |
| 5,929,208 | 7/1999 | Heller et al. | 530/333 |
| 6,051,380 | * 4/2000 | Sosnowski et al. | 435/6 |

* cited by examiner

Primary Examiner—Ardin H. Marschel
(74) Attorney, Agent, or Firm—Lyon & Lyon LLP

(57) ABSTRACT

The present invention pertains to a method of, and a device created by, depositing an inorganic permeation layer on a micro-electronic device for molecular biological reactions. The permeation layer is preferably sol-gel. The sol-gel permeation layer can be created with pre-defined porosity, pore size distribution, pore morphology, and surface area. The sol-gel permeation layer may also function as the attachment layer of the micro-electric device.

24 Claims, 8 Drawing Sheets

SOL-GEL PERMEATION LAYER WITH AGAROSE

SOL-GEL PERMEATION LAYER WITH AGAROSE

SOL-GEL PERMEATION LAYER WITH COVALENT ATTACHMENT OF CAPTURE PROBE

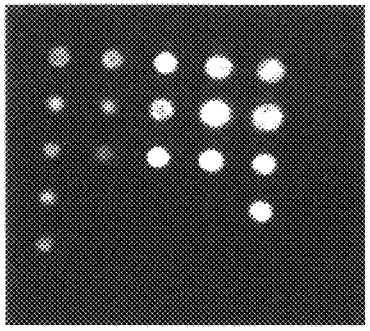

FIG. 8

Thin agarose/streptavidin on thick sol-gel
Capture Load with 20 nM biotin-T12-BTR
Sol-Gel sample a242e_02_04

Reverse Dot Hybridization - ATA.5/RCA.5

FIG. 7

| Conditions | | | | |
|---|---|---|---|---|
| 200 nA, 2min | 200 nA, 2min | 400 nA, pulse | 200 nA, 4 min | 200 nA, 4 min |
| 200 nA, pulse | 200 nA, pulse | 400 nA, pulse | 400 nA, 2 min | 400 nA, 2 min |
| 200 nA, pulse | 200 nA, pulse | 400 nA, pulse | 400 nA, pulse | 400 nA, pulse |
| 200 nA, pulse | none | none | none | 400 nA, pulse |
| 200 nA, pulse | none | none | none | none |

Results (MFI/sec)

| | | | | |
|---|---|---|---|---|
| 2739.7 | 3223.46 | 7303.89 | 4833.02 | 4507.12 |
| 2736.55 | 2432.76 | 3869.68 | 4910.55 | 4361.04 |
| 2410.51 | 1812.5 | 6061.99 | 7301.65 | 5521.96 |
| 2360.5 | 500.14 | 536.48 | 566.61 | 6097.33 |
| 2191.22 | 466.62 | 502.07 | 517.45 | 512.36 |

Capture Load - Columns 1, 3, 5 w/500 nM ATA.5, Columns 2,4 w/500 nM ATA.4
Loading at a pulsed 400 nA per pad program; # of points listed below

| | | | | |
|---|---|---|---|---|
| 1800 | 900 | 900 | 900 | 900 |
| 1800 | 900 | 900 | 900 | 900 |
| 1800 | 900 | 900 | 900 | 900 |
| 1800 | N/A | N/A | 900 | 900 |
| 1800 | N/A | N/A | N/A | 900 |

Target address - 400 nA pulse per pad, 0.1 sec ON, 0.2 sec OFF, 1000pts.
20nM RCA.5-BTR
Results:

| | | | | |
|---|---|---|---|---|
| 223.23 | 152.75 | 259.58 | 165.04 | 207.27 |
| 201.95 | 155.39 | 261.19 | 163.37 | 210.47 |
| 199.1 | 165.99 | 315.9 | 168.12 | 193.91 |
| 228.18 | 138.23 | 136.11 | 147.53 | 254.02 |
| 261.76 | 137.52 | 137.38 | 137.48 | 254.87 |

Column 1 vs. Column 2        Column 3,5 vs. Column 4
Sp/NSp =    1.41              Sp/NSp =    1.48

Passive hybridization, 2% CTAB
- APS treated sol-gel
- ACA5-ribo-U (1.71 $\mu$M)
 PH 7.4
 Attachment time: 24 hrs.
- RCA5-BTR (10 $\mu$M)
 Incubation time: 15 min.
10 secretary integration (C3):
On pads: Average. MFI = 6760
Off pads: Average. MFI = 3750

INORGANIC PERMEATION LAYER FOR MICRO-ELECTRIC DEVICE

This application is a continuation-in-part of U.S. application Ser. No. 08/986,065, filed Dec. 5, 1997, now U.S. Pat. No. 6,051,380; which is a continuation-in-part of U.S. application Ser. No. 08/534,454, filed Sep. 27, 1995, now U.S. Pat. No. 5,849,486; which is a continuation-in-part of U.S. application Ser. No. 08/304,657, filed Sep. 9, 1994, now U.S. Pat. No. 5,632,957 (which has been continued as application Ser. No. 08/859,644, filed May 20, 1997), which is a continuation-in-part of Ser. No. 08/271,882, filed Jul. 7, 1994, now U.S. Pat. No. 6,017,696; which is a continuation-in-part of Ser. No. 08/146,504, filed Nov. 1, 1993, now U.S. Pat. No. 5,605,662, and a continuation-in-part of Ser. No. 08/708,262, filed Sep. 6, 1996; abandoned.

FIELD OF THE INVENTION

This invention pertains to the design fabrication, and uses of a self-addressable. self-assembling microelectronic system which can actively carry out and control multi-step and multiplex reactions in microscopic formats. In particular, these reactions include molecular biological reactions, such as nucleic acid hybridizations, antibody/antigen reactions, clinical diagnostics, and biopolymer synthesis. More specifically, the invention relates to an inorganic permeation layer for the microelectric device.

BACKGROUND OF THE INVENTION

Sol-gel has been employed as a monolithic gel deposition on a variety of substrates. See, for example, U.S. Pat. No. 4,652,467 and U.S. Pat. No. 5,224,972, both issued to Brinker et al. In this process, metal alkoxides of network forming cations, e.g., Si, Al, B, Ti, P, and optionally soluble salts of modifying cations, are used as glass precursors. In alcoholic solutions catalyzed by additions of acid or base, the alkoxides are partially or completely hydrolyzed and then polymerized to form molecules of glass-like oxide networks linked by bridging oxygen atoms. This technique is readily adapted to preparation of multicomponent oxide solutions as well as single component systems.

The net reactions which describe this process are generally represented as:

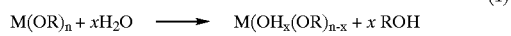

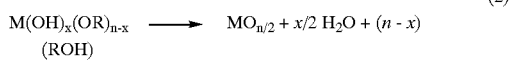

where x in reaction 1 can be varied, e.g., from about 1–20. Generally, reaction 2 does not go to completion, i.e., colloidal particles of anhydrous oxides do not result. When the growing polymers link together to form an infinite network, the solution stiffens to a gel.

The chemistry involved in the formation of these monolithic gels is well documented in the prior art. See, e.g., (1) Brinker et al, "Sol-gel Transition in Simple Silicates", J. Non-Cryst. Solids, 48 (1982) 47–64; (2) Brinker et al, "Sol-gel Transition in Simple Silicates II", J. Non-Cryst. Solids, 63 (1984) 45–59; (3) Schaefer et al, "Characterization of Polymers and Gels by Intcnediatc Anglc X-ray Scattering", presented at the International Union of Purc and Applied Chemists MAC-RO'82, Amherst, Mass., Jul. 12, 1982; (4) Pettit et al, Sol-Gcl Protective Coatings for Black Chrome Solar Selective Films, SPIE Vol. 324, Optical Coatings for Energy Efficiency and Solar Applications, (pub. by the Society of Photo-Optical Instrumentation Engineers, Bellingham, Wash.) (1982) 176–183; (5) Brinker et al, "Relationships Between the Sol to Gel and Gel to Glass Conversions", Proceedings of the International Conference on Ultrastructure Processing of Ceramics, Glasses, and Composites, (John Wilcy and Sons, N.Y.) (1984); (6) Brinker et al, "Conversion of Monolithic Gels to Glasses in a Multicomponent Silicate Glass System", J. Materials Sci., 16 (1981) 1980–1988; (7) Brinker et al, "A Comparison Between the Densification Kinetics of Colloidal and Polymeric Silica Gels", Mat. Res. Soc. Symp. Proc. Vol. 32 (1984), 25–32; all of which disclosures are entirely incorporated by reference wherein. For example, much work has been done in characterizing the relationship between the properties of a monolithic, bulk gel prepared by these systems and of the properties of the solution from which such gel is made. For instance, the relationship between solution characteristics such as pH and water content for a given solution chemical composition and the size and nature of the polymer which results in solution, and the relationship between such polymer properties and the characteristics of the finally produced gel, e.g., the degree of crosslinking, the porosity of the gel, etc., have been well studied and discussed in these references.

The fact that gel formation can be retarded by making the solutions sufficiently dilute, e.g., less than 10% equivalent oxides, is known. In such dilutions, more typically 2–5% equivalent oxides, the solution can be applied to various substrates by conventional processes. Under such circumstances, the partially hydrolyzed glass-like polymers react chemically with the substrate surface, thereby achieving complete wetting.

The physical properties of sol-gel materials are tailored through stoichiometry, aging, drying conditions and method of deposition. Emphasis for examining these parameters has been on silicate-based systems, which has led to microporous monoliths and thin films (pore size <2 nm). The most prominent applications of sol-gel synthesis have been the development of mesoporous (pore size from 2 nm to 50 nm) materials that possess well-defined pore morphology. To generate this pore morphology, a method known as surfactant templating has been devised. This approach is based on the ability for a ternary system, consisting of water, ethanol and surfactant, to develop a three dimensional structure (or a lyotropic phase) that may be described as cubic, hexagonal, lamellar or isotropic, depending upon the molar ratio of the three components. The formation of these phases is sometimes referred as liquid crystal templating. In general, the introduction of a hyrdolyzed silicon alkoxide precursor, once hyrolyzed, infiltrates the water rich regions and forms in inorganic 'shell' around the hydrophobic surfactant. Upon drying and heating in excess of 400° C., the organic surfactant phase is removed, leaving behind the inorganic, silica shell with porosity defined by the once present surfactanit phase. The pore sizes range from 2 nm to 100 nm depending upon the nature of the surfactant. The silica wall thickness ranges from 1 nm to 10 nm, which relies on processing parameters such as aging, pH and temperature.

However, none of the known uses of sol-gel chemistry in thin film deposition contemplates the use of sol-gel as a permeation layer for an electrical micro-array devices. Current permeation layers for electric micro-arrays are organic monomers or polymers with undefined pure size and porosity that swell when exposed to an aqueous solution. The previously not contemplated use of sol-gel as a permeation layer for an electrical micro-assay device solves the above limitations of organic permeation layers by providing a permeation layer that has controllable porosity and pore size and is not susceptible to swelling when exposed to an aqueous solution.

SUMMARY OF THE INVENTION

Current methods for synthesizing permeation layers involve the utilization of monomers or polymers to form a membrane with undefined pore size and porosity. Furthermore, these permeation layers (i.e. agarose and synthetic polymers) may swell when exposed to an aqueous solution.

To circumvent these obstacles, sol-gel processing provides a means for fabricating thin films (up to 1 micron) with predetermined pore size, pore size distribution, pore morphology, surface area and porosity. With these capabilities the sol-gel Support may be tailored to achieve a variety of porous characteristics, suited for a specified application or assay. Since sol-gel materials are based on metal alkoxide precursor chemistry or metal oxide colloidal suspensions, the resulting material is inorganic. Thus, a rigid support is formed that will maintain its physical properties when immersed in aqueous solutions (resistance to swelling) and remain chemically resistant to biological and electrochemically generated products.

Typically, sol-gel chemistry is based upon silicate precursor chemistry, but may be applied to other inorganic systems that include alumina, titania, zirconia, hafnia, germania, borates and phosphates. These systems alone or in combination with silica may be implemented to yield a robust, yet porous sol-gel permeation layer. In addition, sol-gel chemistry is amenable for large-scale manufacturing in which coatings may be applied at the wafer level rather than on the individual chip.

Inorganic membranes synthesized by sol-gel chemistry have been applied as a permeation layer and as a support for attachment chemistry. In both instances, the sol-gel layer acted as a base-layer for the subsequent attachment layer. Attachment layer chemistry includes at least two methods: agarose/streptavidin and direct-attachment to the permeation layer. In the first example, a thin layer of agarose/streptavidin was directly deposited on the sol-gel film. Passive attachment, electronic attachment and reverse dot blot hybridizations were achieved with this permeation and attachment layer configuration. In a second example, the direct attachment of oligonucleotides was attained by bonding the capture probes to the sol-gel, followed by passive hybridization.

BRIEF DESCRIPTION OF THE DRAWINGS

FIG. 7 is a first micro photograph of the capture of oligonuclcotides to the agarose/streptavidin attachment layer of FIG. 6;

FIG. 8 is a second micro photograph of the capture of oligonucleotides to the agarosc/streptavidin attachment layer of FIG. 6.

DETAILED DESCRIPTION OF THE INVENTION

Figure 1:
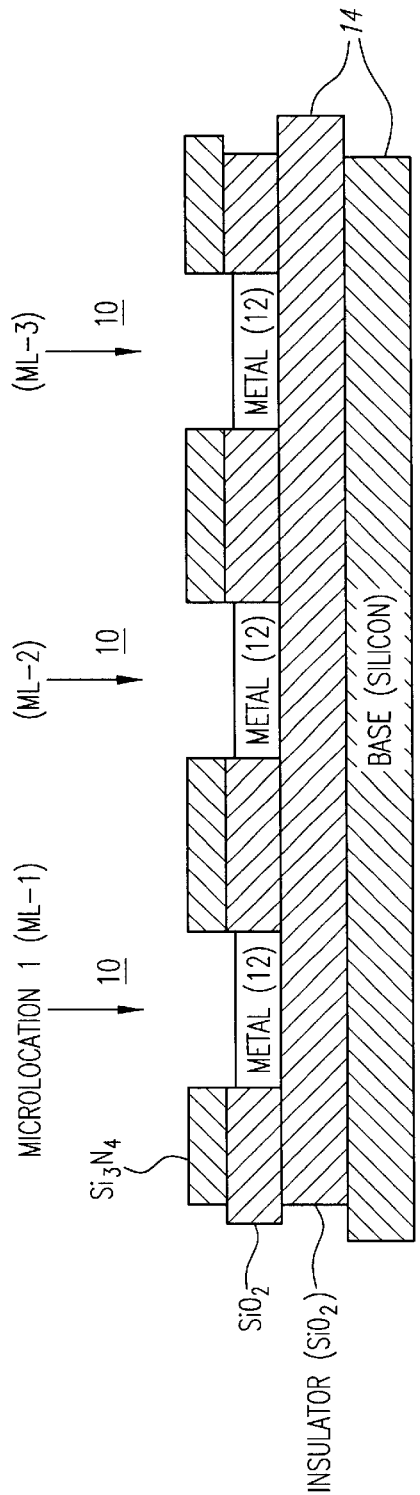
FIG. 1 is the cross-section of three self-addressable micro-locations fabricated using microlithograplic techniques.

The devices and the related methodologies of this invention allow important molecular biology and diagnostic reactions to be carried out under complete electronic control. The basic concept of this invention is a microelectronic device with specially designed addressable microscopic locations. Each micro-location has a derivatized surface for the attachment of specific binding entities (i.e., an attachment layer), a permeation layer, and an underlying direct current (DC) micro-electrode. After the initial fabrication of the basic microelectronic structure, the device is able to self-direct the addressing of each specific micro-location with specific binding entities. The self-addressed device is subsequently able to actively carry out multi-step, combinatorial, and multiplex reactions at any of its micro-locations. The device is able to electronically direct and control the rapid movement and concentration of analytes and reactants to or from any of its micro-locations. The ability of the device to electronically control the dynamic aspects of various reactions provides a number of new and important advantages and improvements.

In order for a device to carry out multi-step and multiplex reactions, its crucial electronic components must be able to maintain active operation in aqueous solutions. To satisfy this requirement, each micro-location must have an underlying functioning DC mode micro-electrode. Other considerations for the design and fabrication of a device include, but are not limited to, materials compatibilities, nature of the specific binding entities and the subsequent reactants and analytes, and the number of micro-locations.

By "a functioning DC mode micro-electrode" is meant a micro-electrode biased either positively or negatively, operating in a direct current mode (either continuous or pulse), which can affect or cause the free field electrophoretic transport of charged specific binding entities, reactants, or analytes to or from any location on the device, or in the sample solution.

Within the scope of this invention, the free field electrophoretic transport of molecules is not dependent on the electric field produced being bounded or confined by dielectrical material.

A device can be designed to have as few as two addressable micro-locations or as many as hundreds of thousands of micro-locations. In general, a complex device with a large number of micro-locations is fabricated using microlithography techniques. Fabrication is carried out on silicon or other suitable substrate materials, such as glass, silicon dioxide, plastic, or ceramic materials. These microelectronic "chip" designs would be considered large scale array or multiplex analysis devices. A device with a small number of micro-locations would be fabricated using micro-machining techniques.

Addressable micro-locations can be of any shape, preferably round, square, or rectangular. The size of an addressable micro-location can be of any size, preferably range from sub-micron (~0.5 $\mu$m) to several centimeters (cm), with 5 $\mu$m to 100 $\mu$m being the most preferred size range for devices fabricated using microlithographic techniques, and 100 $\mu$m to 5 millimeters being the most preferred size range for devices fabricated using the micro-machining techniques. To make micro-locations smaller than the resolution of microlithographic methods would require techniques such as electron beam lithography, ioi beam lithography, or molecular beam epitaxy. While microscopic locations are desirable for analytical and diagnostic type applications, larger addressable locations (e.g., larger than 2 mm) are desirable for preparative scale biopolymer synthesis.

After micro-locations have been created by using microlithographic and/or micro-machining techniques, chemical techniques are used to create the specialized attachment and permeation layers which would allow the DC mode micro-electrodes under the micro-locations to: (1) affect or cause the free field electrophoretic transport of specific (charged) binding entities from any location; (2) concentrate and covalently attach the specific binding, entities to the specially modified surface of the specific micro-location; and (3) continue to actively function in the DC mode after the attachment of specific binding entities so that other reactants and analytes can be transported to or from the micro-locations.

A. Design Parameters

FIG. 1 shows a basic design of self-addressable micro-locations fabricated using microlithographic techniques. The three micro-locations (10) (ML-1, ML-2, ML-3) are formed on the surface of metal sites (12) which have been deposited on an insulator layer/base material. The metal sites (12) serve as the underlying micro-electrode structures (10). An insulator material separates the metal sites (12) from each other. Insulator materials include, but are not limited to, silicon dioxide, glass, resist, rubber, plastic, or ceramic materials.

Figure 2:
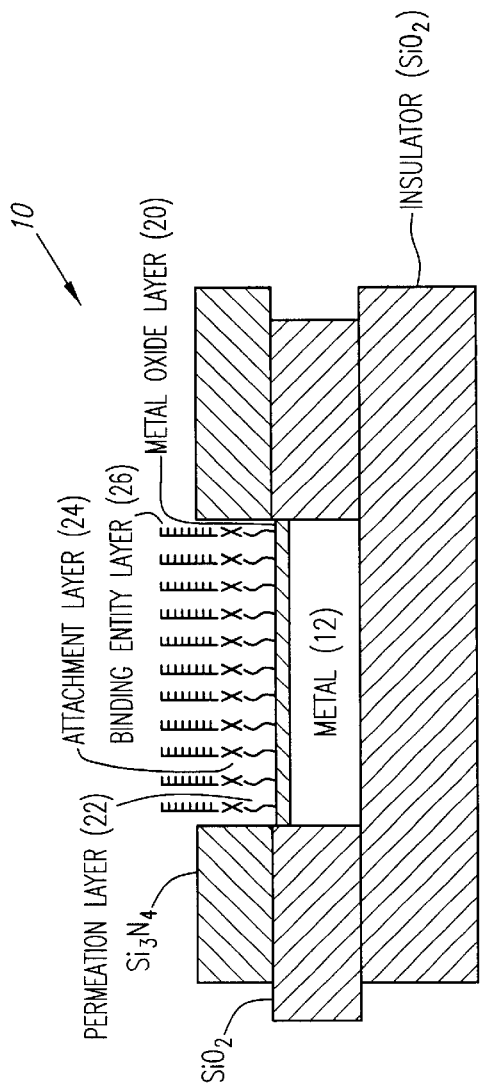
FIG. 2 is the cross-section of a microlithographically fabricated micro-location.

FIG. 2 shows the basic features of an individual micro-location (10) formed on a microlithographically produced metal site (12). The addressable micro-location is formed on the metal site (12), and incorporates an oxidation layer (20), a permeation layer (22), an attachment layer (24), and a binding entity layer (26). The metal oxide layer provides a base for the coupling of the permeation layer. The permeation layer provides spacing between the metal surface and the attachment/binding entity layers and allows solvent molecules, small counter-ions, and gases to freely pass to and from the metal surface. The thickness of the permeation layer for microlithographically produced devices can range from approximately 1 nanometer (nm) to 10 microns ($\mu$m), with 2 nm to 1 $\mu$m being the most preferred. The attachment layer provides a base for the binding of the binding entities. The thickness of the attachment layer for microlithographically produced devices can range from 0.5 nm to 1 $\mu$m, with 1 nm to 200 nm being the most preferred. In some cases, the permeation and attachment layers can be formed from the same material. The specific binding entities are covalently coupled to the attachment layer, and form the specific binding entity layer. The specific bindings entity layer is usually a mono-layer of the specific binding molecules. However, in some cases the binding entity layer can have several or even many layers of binding molecules.

Certain design and functional aspects of the permeation and attachment layer are dictated by the physical (e.g., size and shape) and the chemical properties of the specific binding entity molecules. They are also dictated to some extent by the physical and chemical properties of the reactant and analyte molecules, which will be subsequently transported and bound to the micro-location. For example, oligonucleotide binding entities can be attached to one type of micro-location surface without causing a loss of the DC mode function, i.e., the underlying micro-electrode can still cause the rapid free field electrophoretic transport of other analyte molecules to or from the surface to which the oligonuclcotide binding entities are attached. However, it large globular protein binding entities (e.g., antibodies) arc attached to the same type of surface, they may effectively insulate the surface and cause a decrease or a complete loss of the DC mode function. Appropriate modification of the attachment layer would have to be carried out so as to either reduce the number of large binding entities (e.g., large globular proteins) or provide spacing between the binding entities on the surface.

The spacing between micro-locations is determined by the ease of fabrication, the requirement for detector resolution between micro-locations, and the number of micro-locations desired on a device. However, particular spacings between micro-locations, or special arrangement or geometry of the micro-locations is not necessary for device function, in that any combination of micro-locations (i.e., underlying micro-electrodes) can operate over the complete device area. Nor is it necessary to enclose the device or confine the micro-locations with dielectric boundaries. This is because complex electronic field patterns or dielectric boundaries are not required to selectively move, separate, hold, or orient specific molecules in the space or medium between any of the electrodes. The device accomplishes this by attaching the specific binding molecules and subsequent analytes and reactants to the surface of an addressable micro-location. Free field electrophoretic propulsion provides for the rapid and direct transport of any charged molecule between any and all locations on the device.

As the number of micro-locations increases beyond several hundred, the complexity of the underlying circuitry of the micro-locations increases. In this case the micro-location grouping patterns have to be changed and spacing distances increased proportionally, or multi-layer circuitry can be fabricated into the basic device.

In addition to micro-locations which have been addressed with specific binding entities, a device will contain some un-addressed, or plain micro-locations which serve other functions. These micro-locations can be used to store reagents, to temporarily hold reactants or analytes, and as disposal units for excess reactants, analytes, or other interfering components in samples. Other un-addressed micro-locations can be used in combination with the addressed micro-locations to affect or influence the reactions that are occurring at these specific micro-locations. These micro-locations add to intra-device activity and control. It is also possible for the micro-locations to interact and transport molecules between two separate devices. This provides a mechanism for loading a working device with binding entities or reactants from a storage device, and for copying or replicating a device.

Figure 3:
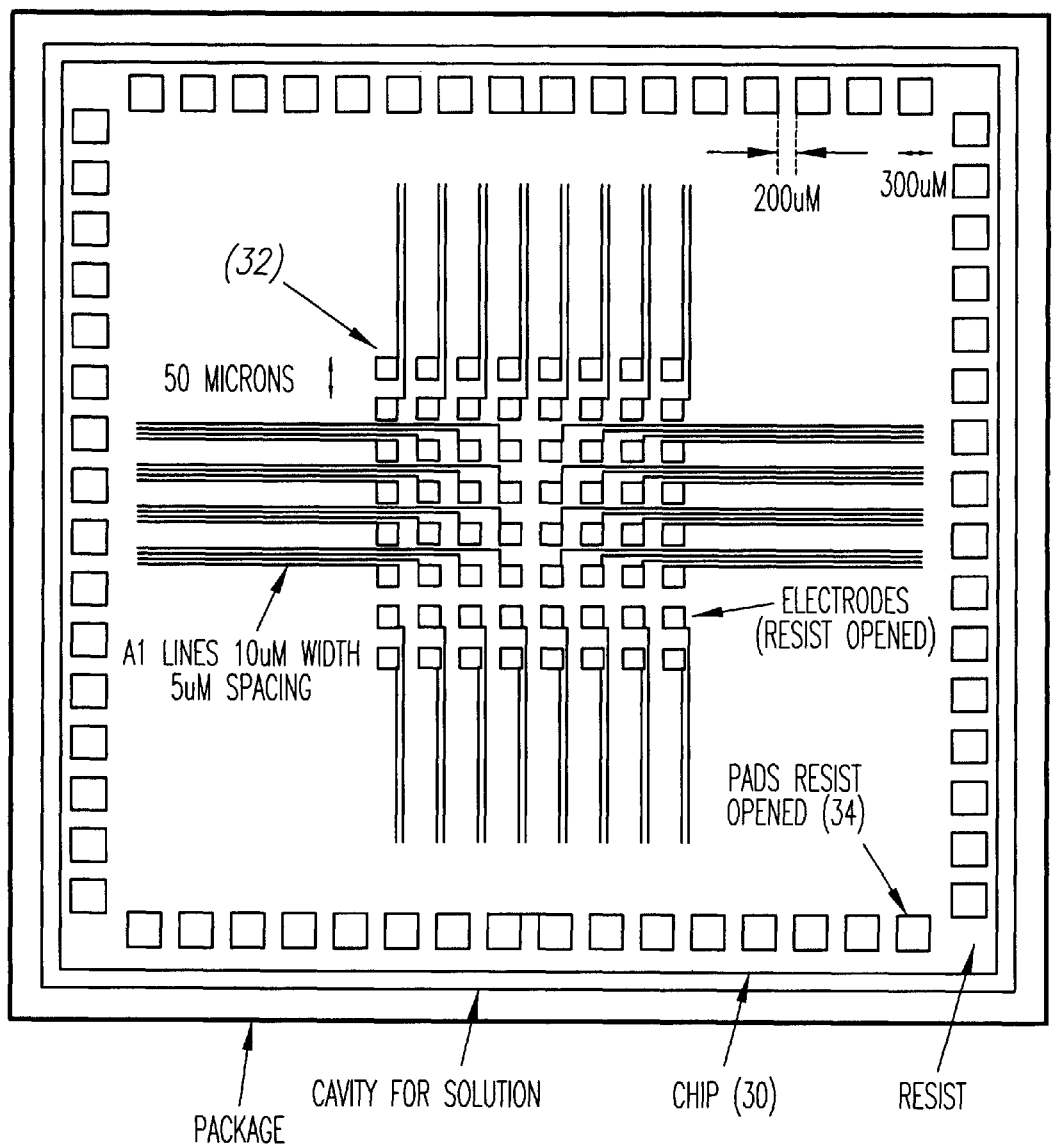
FIG. 3 is a schematic representation of a self-addressable 64 micro-location chip which was actually fabricated, addressed with oligonucleotides, and tested.

FIG. 3 shows a matrix type device containing 64 addressable micro-locations (30). A 64 micro-location device is a convenient design, which fits with standard microelectronic chip packaging components. Such a device is fabricated on a silicon chip approximately 1 cm×1 cm, with a central area approximately 750 µm×750 µm containing the 64 micro-locations. Each micro-location (32) is approximately 50 µm square with 50 µm spacing between neighboring micro-locations. Connective circuitry for each individual underlying micro-electrode runs to an outside perimeter (10 mm×10 mm) of metal contact pads (300 µm square) (34). A raised inner perimeter can be formed between the area with the micro-locations and the contact pads, producing a cavity which can hold approximately 2 to 10 microliters (µl) of a sample solution. The "chip" can be mounted in a standard quad package, and the chip contact pads (34) wired to the quad package pins. The packaged chip can then be plugged into a microprocessor controlled DC power supply and multimeter apparatus which can control and operate the device.

B. Fabrication Procedures
1. Microlithography Fabrication Steps

General microlithographic or photolithographic techniques can be used for fabrication of the complex "chip" type device, which has a large number of individually addressable microelectrodes. The conventional electronics for addressing these electrodes can be located on the chip in the form of an integrated circuit or off the chip on a printed circuit board. While the fabrication of an array of microelectrodes does not require complex photolithography, the selection of materials requires special considerations in order for such electrodes to operate in an aqueous environment.

The devices like the sixty-four microelectrodes device (30) shown in FIG. 3 can be fabricated using relatively simple mask designs and standard microlithographic techniques. Generally, the base substrate material would be a 4-inch diameter silicon wafer, approximately 20 mils thick. For fabricating microelectrodes arrays whose electronic addressing is controlled off chip, the first processing step is to grow an insulating thermal silicon dioxide 0.5 to 1.0 microns into the wafer. In the case of fabricating platinum silicide (PtSi) electrodes a thin layer (~50 nm) of amorphous silicon (a-Si) is deposited over the surface of the wafer by means of a sputter deposition system. Using standard optolithography techniques, photo resist would be spun onto the wafer (i.e., Shippley Photo Resist 3612) and then exposed with the negative image of the metal wiring defining the electrodes, the wire bond pads, and the metal traces connecting the electrodes to the wire bond pads. After the photo resist is removed and a thin layer (~50 nm) of platinum (Pt) is sputter deposited over the entire surface of the wafer. The Pt and patterned a-Si are alloyed together in a tube furnace, forming PtSi. The unalloyed Pt is then removed using an aqua regia etch, leaving only the patterned PtSi. At this point an electronically insulating top dielectric (either silicon dioxide ($SiO_2$) or silicon nitride ($Si_xN_y$) or a combination of the two) is deposited over the entire wafer by means of a Plasma Enhanced Vapor Deposition (PECVD) system. Again standard photolithography techniques are used to pattern openings in photo resist above electrodes and the wire bond pads, and again a plasma etcher is used to etch down through the top dielectric to the PtSi. At this point the wafer can be diced into individual chips.

The bottom dielectric (thermal $SiO_2$) electrically insulates the PtSi from the silicon substrate, while the top dielectric (PECVD $SiO_2$ and/or $Si_xN_y$) electrically insulates the wire traces from the aqueous solution. Other metal systems other than PtSi can be used to fabricate the electrodes (i.e., Ti—Pt, TiW—Pt, Ti—Au, Ti—Pd, C) and would have processing steps consistent with patterning techniques for those material systems. In the case of the electro-deposited permeation layers, the ideal material system is a PtSi metalization and a layer of PECVD $SiO_2$ covered by a layer of PECVD $Si_xN_y$ for the top dielectric. The PtSi provides $Si/SiO_2$ attachment sites on the surface of the electrode for the permeation layer. The PECVD $SiO_2$ provides attachment sites to the dielectric well walls while the PECVD $Si_xN_y$ provides a dense ion barrier that inhibits the DNA attachment chemistry used on the permeation layer.

2. Permeation and Attachment Layer Formation Steps

At this point the micro-electrode locations on the device are ready to be modified with specialized permeation and attachment layers. The objective is to create on the micro-electrode an intermediate permeation layer with selective diffusion properties and an attachment surface layer with optimal binding properties. The attachment layer should have from $10^5$ to $10^7$ functionalized locations per square micron ($\mu m^2$) for the optimal attachment of specific binding entities. However, the attachment of specific binding entities must not overcoat or insulate the surface so as to prevent the underlying micro-electrode from functioning. A functional device requires some fraction (~5% to 25%) of the actual metal micro-electrode surface to remain accessible to solvent ($H_2O$) molecules, and to allow the diffusion of ions (e.g., $H^+$ and $OH^-$) and electrolysis gases (e.g., $O_2$ and $H_2$) to occur.

The intermediate permeation layer must also allow diffusion to occur. Additionally, the permeation layer should have a pore limit property which inhibits or impedes the larger binding entities, reactants, and analytes from physical contact with the micro-electrode surface. The permeation layer keeps the active micro-electrode surface physically distinct from the binding entity layer of the micro-location device.

In terms of the primary device function, this design allows the electrolysis reactions required for electrophoretic transport to occur on micro-electrode surface, but avoids adverse electrochemical effects to the binding entities, reactants, and analytes. Sol-gel has been found to have benefits as a permeation layer not present in organic compounds, including pre-defined porosity, pore size, pore size distribution, pore morphology and surface area.

The sol-gel compositions are comprised of tetraethyl orthosilicate, ethanol, deionized water, hydrochloric acid and surfactant. Specifically, tetraethyl orthosilicate, sub-stoichiometric concentration of water, 200 proof ethanol, and hydrochloric acid are added to a boiling flask in the above listed order:

Preparation of stock solution:

| Volume | Molar Ratio |
| --- | --- |
| 61 mL Tetraethyl orthosilicate (Aldrich) | 1.0 |
| 61 mL absolute ethanol (200 proof, Quantum) | 4.0 |
| 4.87 mL de-ionized water (Milli-Q) | 1.0 |
| 0.2 mL 0.07M HCl | $5 \times 10^{-5}$ |

The solution is refluxed at 60° C. for 90 minutes while magnetically stirling. After cooling this "stock solution" to room temperature, a portion of the partially hydrolyzed metal alkoxide solution may be extracted and mixed with additional deionized water and HCl:

| Volume | | | |
|---|---|---|---|
| 34.5 mL stock solution | | | |
| 1.38 mL de-ionized water | | | |
| 4.14 mL 0.07M HCl | | | |
| Final Preferred Molar Ratio | | Final Molar Ratio Range | |
| TEOS | 1.0 | TEOS | 1.0 |
| $H_2O$ | 5.1 | $H_2O$ | 1.0–40.0 |
| EtOH | 22 | EtOH | 0.0–40.0 |
| HCl | 0.0039 | HCl | 0.0001–0.1 |

After these components are mixed for 15 minutes, the solution is diluted with ethanol in a ratio of 2:1 (2 pails ethanol to 1 part sol-gel solution). To generate the appropriate pore size, a surfactant such as cetyltrimethylammonium bromide (or CTAB) may be added to the solution. The concentration of CTAB ranges from 1 wt. to 5 wt. % depending upon the desired pore morphology. Once the surfactant has completely dissolved, the sol is ready for deposition by spin coating. The chips are spin coated for 20 sec. to 30 sec. at a rate that ranges from 1500 rpm to 6000 rpm. Prior deposition of the liquid onto the chip, however, the solution is passed through a 0.2 μm filter. After spin coating, the chips are placed in a furnace and heated at a rate of 1° C./min until 450° C. is attained. The temperature is held at this point for 3 hours before slowly cooling to room temperature. The sol-gel film that remains consists of more than 99% $SiO_2$. The average pore size of the sol-gel films was estimated to be 25 Å according to TEM evaluation of films prepared with similar compositions.

Figure 6:
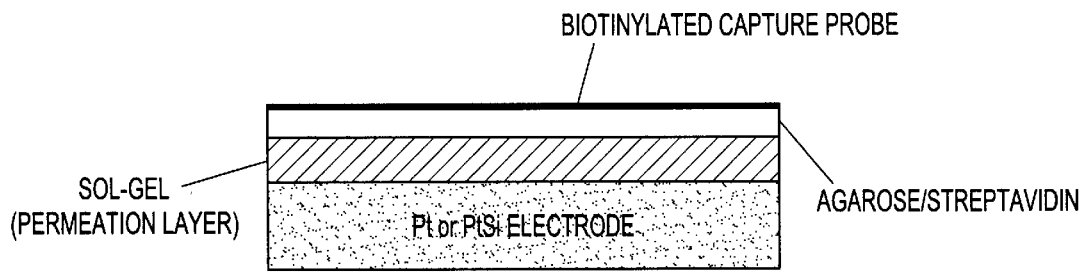
FIG. 6 is a schematic of a sol-gel permeation layer and an agarose/streptavidin attachment layer.

Subsequently, the surface of this material may be functionalized by silanization techniques to provide favorable attachment chemistries. In a first iteration, as shown in FIG. 6, a thin layer of agarose/streptavidin was deposited onto a ~500 nm thick sol-gel coating. As shown in FIG. 7, by applying the established biotinstreptavidin attachment chemistry BODIPY-Texas Red labeled oligonucleotides ($T_{12}$) were electronically bound to the agarose layer in a capture loading experiment with a 20 nanomolar biotinylated capture probe. Columns 1, 2 and 5 of FIG. 7 show specific hybridization, columns 2 and 4 show non-specific hybridization. In an ensuing experiment as shown in FIG. 8, a reverse dot blot assay was performed with ATA5-RCA5, thus demonstrating that this dual layer of sol-gel/agarose is feasible. In this example, fluorescently labeled capture oligonucleotides (modified with biotin) were electronically addressed to specified electrodes, which attached to the agarose/streptavidin layer. The resulting reverse dot hybridizations with ATA5-RCA5 yielded specific to non-specific ratios that ranges from 2 to 5.

Figure 9:
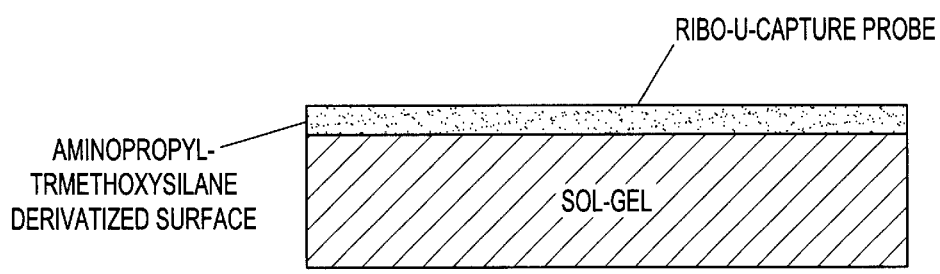
FIG. 9 is a schematic of a sol-gel permeation layer also functioning as an attachment layer.
Figure 10:
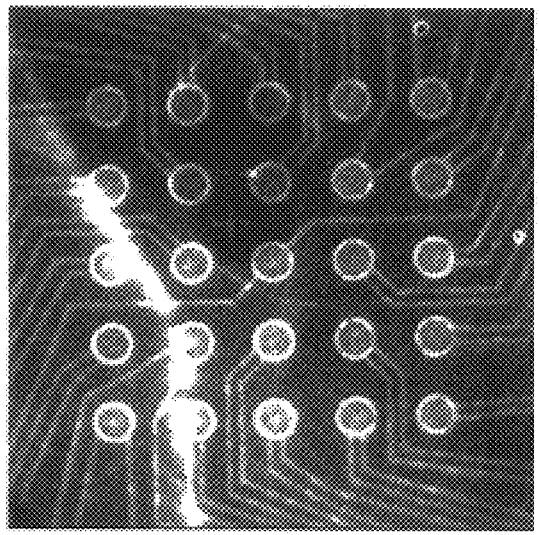
FIG. 10 is a micro photograph of the binding of a ribo-uridine capture probe to the sol-gel layer of FIG. 9.
Figure 11:
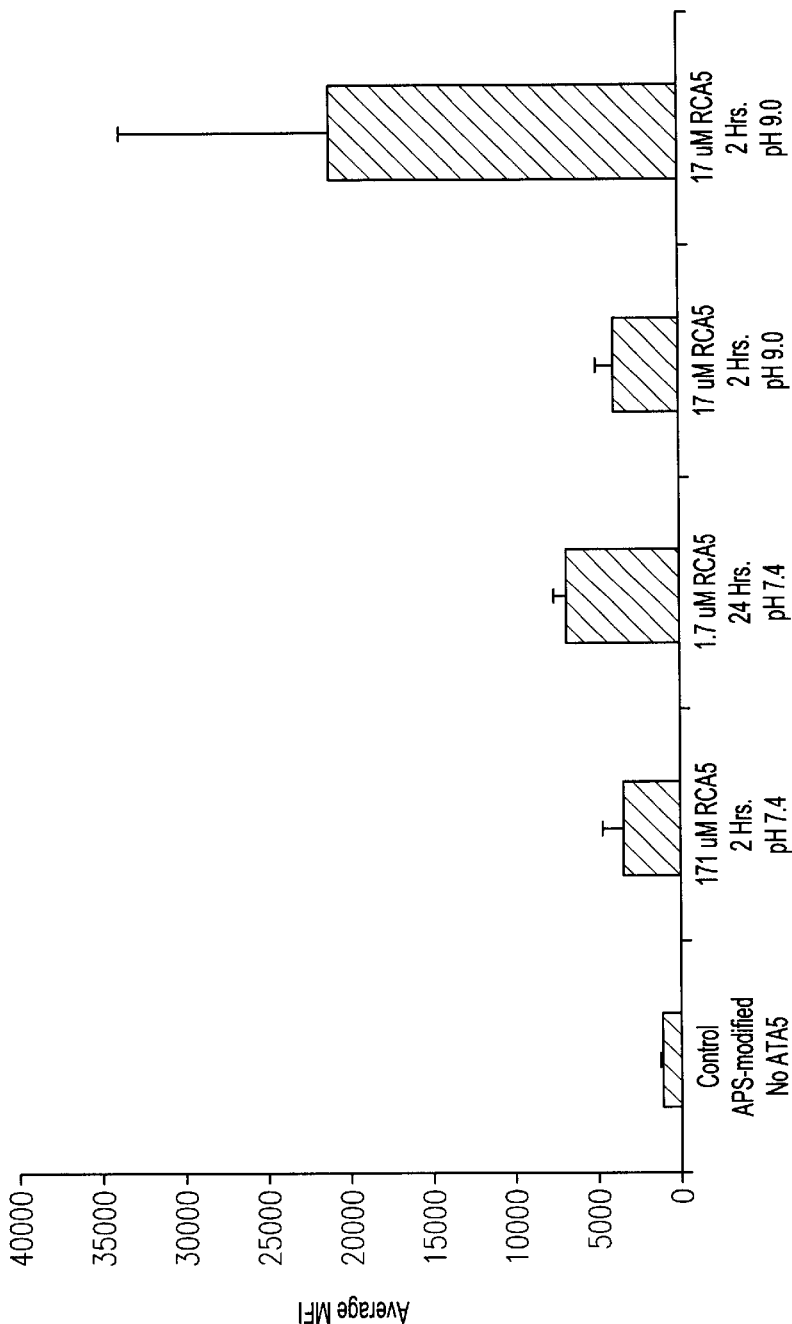
FIG. 11 is a graphical representation of the passive hybridization of the sol-gel permeation layer/attachment layer of FIG. 9.

In FIG. 9, direct attachment of oligonucleotides at either the 3' or 5' end has also been achieved on the sol-gel permeation layer, itself In FIG. 10, an example of direct attachment is provided. Treatment of the sol-gel layer with aminopropyltrimethoxysilane yields a surface covered with amines that can readily bind a fluorescently labeled capture probe modified with ribo-uridine. In this instance, an ATA5-riboU capture probe was attached to the sol-gel surface and then passively hybridized to RCA5-BTR (10 μM). The best results rendered an average of 6760 MFI/sec. FIG. 11 shows a bar graph comparing the passive hybridization (measured by fluorescence) of oligonucleotides directly to the sol-gel permeation layer as a function of concentration, time and pH.

The above data demonstrate the first electric field assisted biological assays performed on a sol-gel substrate, complete with attachment chemistry. In the examples cited above, the sol-gel layer may act as a membrane that permits ionic conduction (agarose) or as an ionic conducting membrane that doubles as a support for the binding of an attachment layer. Surfactant templated sol-gel materials have not been previously employed as a membrane on electrodes for electrochemically addressed reactions or assays. In either case, the porous nature of the sol-gel layer is of utmost importance is controlled via processing conditions and the lyotropic phase formed upon the addition of surfactant. The sol-gel chemistry is not limited to the composition, components and synthesis procedure listed. Instead, numerous formulations are possible and are attributed to the versatility of sol-gel processing. For example, the cited composition is easily modified by altering the following parameters: (1) water to TEOS ration, (2) HCl concentration, (3) type of catalyst (acid or base), (4) concentration of solvent (EtOH), (5) type of precursor, (6) method of synthesis (i.e., use a one step catalysis procedure instead of the two-step procedure) and (7) pH value. Since sol-gel synthesis is performed in the liquid phase, the addition of components such as surfactants, drying control agents, organic/inorganic dopants, organically modified precursors, non-silicate based precursors and polymers may be included in the batch process.

The modification of sol-gel materials is not limited to inorganic precursors (alumina, titania, etc.). If additional mechanical and chemical properties, such as flexibility and hydrophobicity, respectively, are sought then organically modified silicate precursors may be introduced. This class of compounds includes metal alkoxide or metal halide precursors that have at least one moiety that is a non-oxide group (i.e., a Si—C bond). Most of the organically modified precursors employ an alkyl group bonded to the Si atom. This alkyl group may stand alone as an alkyl group such as ethyltrimethoxysilaic or may provide an additional functional group such as an epoxy in 3-glycidoxypropyltrimethoxysilane. If these organic groups are introduced, however, the heating temperature will be greatly reduced to preserve these functionalities.

3. Self-Directed Addressing Of The Devices

The devices are able to electronically self-address each micro-location with a specific binding entity. The device itself directly affects or causes the transport and attachment of specific binding entities to specific micro-locations. The device self-assembles itself in the sense that no outside process, mechanism, or equipment is needed to physically direct, position, or place a specific binding entity at a specific micro-location. This self-addressing process is both rapid and specific, and can be carried out in either a serial or parallel manner.

Figure 4A:
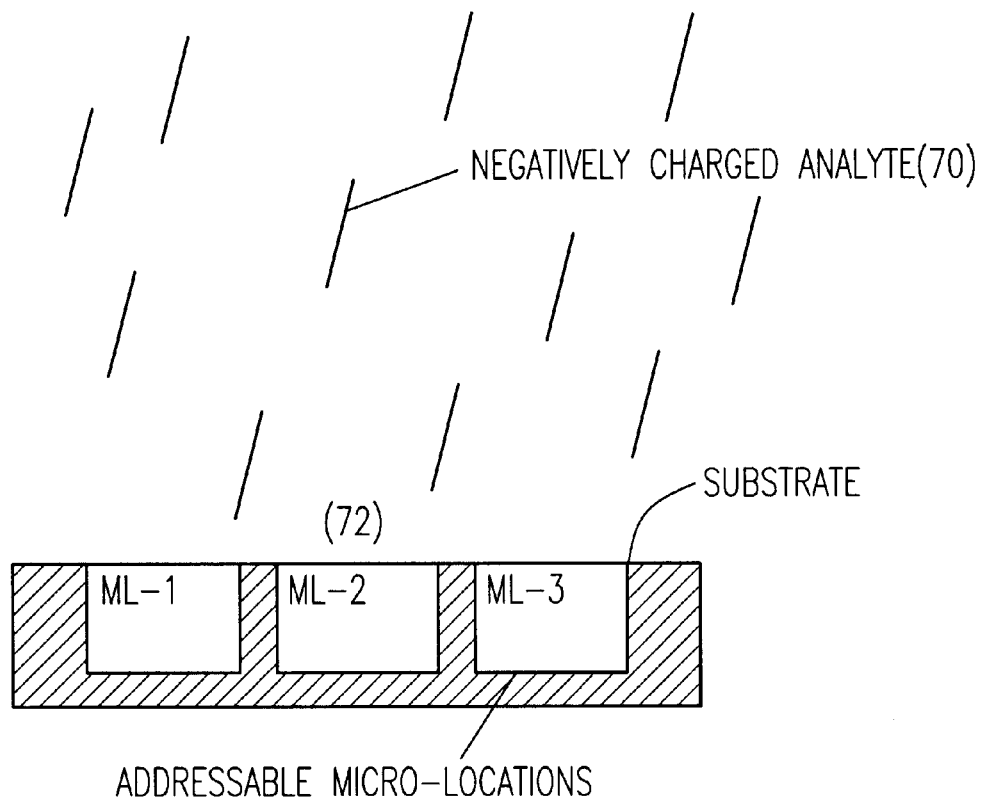
FIGS. 4A and 4B show the mechanism the device uses to electronically concentrate analyte or reactant molecules at a specific micro-location.
Figure 4B:
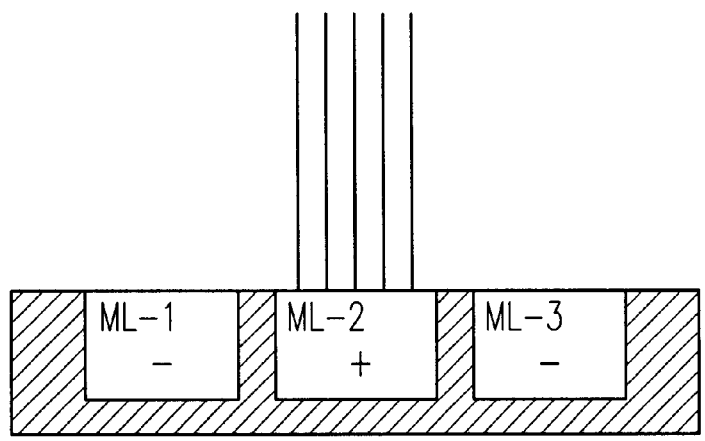
Figure 5A:
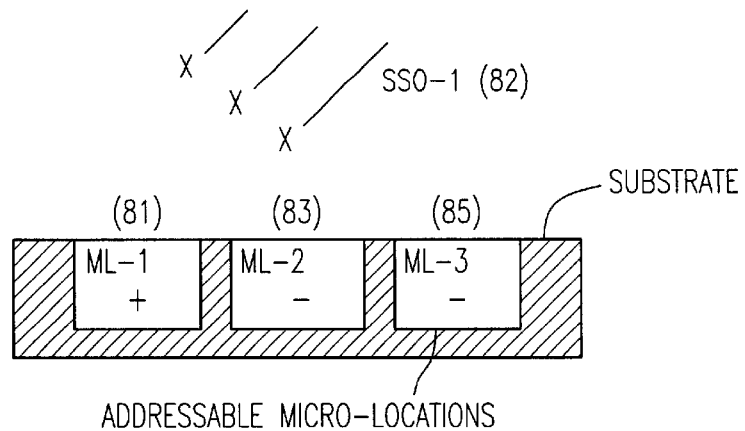
FIGS. 5A, 5B, 5C and 5D show the self-directed assembly of a device with three specific oligonucleotide binding entities (SSO-A, SSO-B, and SSO-C)
Figure 5B:
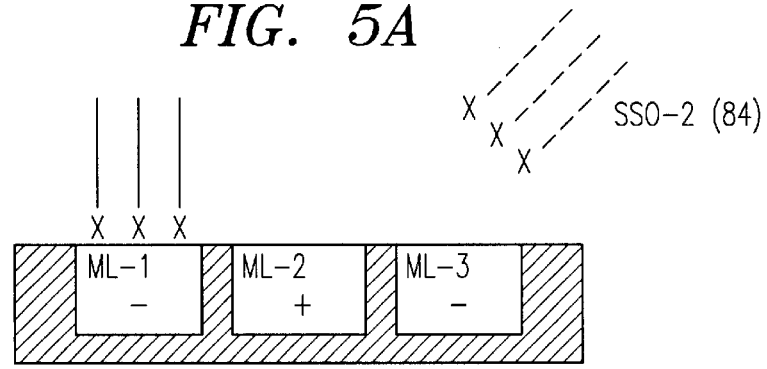
Figure 5C:
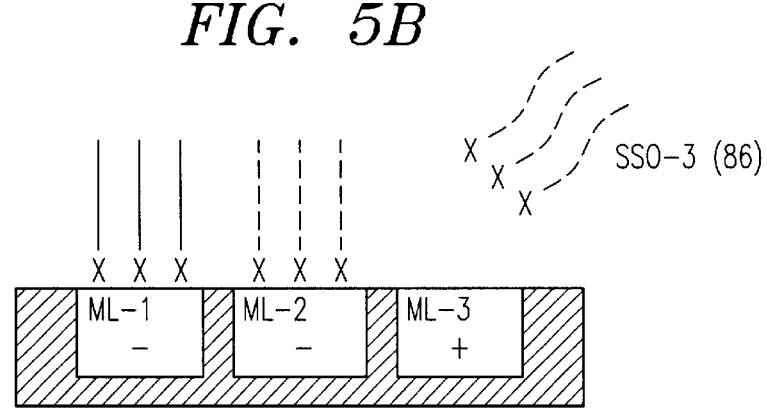
Figure 5D:
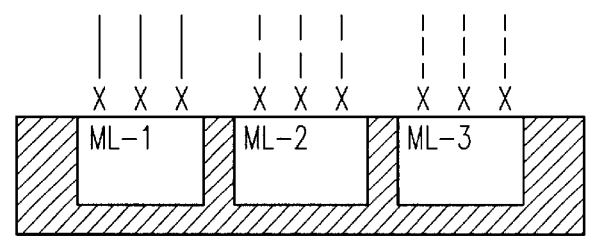

A device can be serially addressed with specific binding entities by maintaining the selected micro-location in a DC mode and at the opposite charge (potential) to that of a specific binding entity. All other micro-locations are maintained at the same charge as the specific binding entity. In cases where the binding entity is not in excess of the attachment sites on the micro-location, it is necessary to activate only one other micro-electrode to affect the electrophoretic transport to the specific micro-location. The specific binding entity is rapidly transported (in a few seconds, or preferably less than a second) through the solution, and concentrated directly at the specific micro-location where it immediately becomes bonded to the special surface. The ability to electronically concentrate reactants or analytes (70) on a specific micro-location (72) is shown in FIGS. 4a and 4b. All other micro-locations remain unaffected by that specific binding entity. Any unreacted binding entity is removed by reversing the polarity of that specific micro-location, and electrophoresing it to a disposal location. The cycle is repeated until all desired micro-locations are addressed with their specific binding entities. FIGS. 5a through 5b show the serial process for addressing specific micro-locations (81, 83, 85) with specific oligonucleotide binding entities (82, 84, 86).

The parallel process for addressing micro-locations simply involves simultaneously activating a large number (particular group or line) of micro-electrodes so that the same specific binding entity is transported, concentrated, and reacted with more than one specific micro-locations.

We claim:

1. An electronic device adapted to receive a solution comprising:
   a substrate;
   a plurality of selectively addressable electrodes on the substrate;
   a permeation layer overlying the electrodes, the permeation layer being
   a sol-gel composition; and
   an electric source for selectively addressing the electrodes.

2. The electronic device of claim 1 wherein the sol-gel composition is comprised of silicon dioxide.

3. The electronic device of claim 2 wherein the silicon dioxide sol-gel composition is formed from tetraethyl orthosilicate, ethanol, de-ionized water, hydrochloric acid and a surfactant.

4. The electronic device of claim 3 wherein the surfactant is cetyltrimethylammonium bromide.

5. The electronic device of claim 3 wherein the concentration of the surfactant is selected from 1 weight percent to 5 weight percent to generate a predetermined pore size in the sol-gel.

6. The electronic device of claim 1 further comprising:
   an attachment layer overlying the permeation layer and having selective binding properties for specific binding entities.

7. The electronic device of claim 1 further comprising:
   an attachment layer integral with the permeation layer and having selective binding, properties for specific binding entities.

8. An electronic device adapted to receive a solution comprising:
   a substrate;
   a plurality of selectively addressable electrodes on the substrate; and
   a permeation layer overlying the electrodes, the permeation layer being a silicon dioxide composition.

9. The electronic device of claim 8 wherein the silicon dioxide composition is formed from tetraethyl orthosilicate, ethanol, de-ionized water, hydrochloric acid and a surfactant.

10. The electronic device of claim 9 wherein the surfactant is cetyltrimethylammonium bromide.

11. The electronic device of claim 9 wherein the concentration of the surfactant is selected from 1 weight percent to 5 weight percent to generate a predetermined pore size in the silicon dioxide composition.

12. The electronic device of claim 8 further comprising:
    an attachment layer overlying the permeation layer with selective binding properties for specific binding entities.

13. The electronic device of claim 8 further comprising:
    an attachment layer integral with the permeation layer and having selective binding properties for specific binding entities.

14. A method for forming an electronic device adapted to receive a solution comprising:
    providing a substrate;
    locating a plurality of selectively addressable electrodes on the substrate; and
    forming a permeation layer overlying the electrodes, the permeation layer being a sol-gel composition.

15. The method of claim 14 wherein the sol-gel composition is comprised of silicon dioxide.

16. The method of claim 15 wherein the silicon dioxide sol-gel composition is formed from tetraethyl orthosilicate, ethanol, de-ionized water, hydrochloric acid and a surfactant.

17. The method of claim 16 wherein the surfactant is cetyltrimethylammonium bromide.

18. The method of claim 16 wherein the concentration of the surfactant is selected from 1 weight percent to 5 weight percent to generate a predetermined pore size in the sol-gel.

19. The method of claim 14 further comprising:
    forming an attachment layer overlying the permeation layer with selective binding properties for specific binding entities.

20. A method of forming a permeation layer for use on an electronic device comprising:
    mixing tetraethylorthosilicate, an alcohol, water and an acid to form a stock solution;
    mixing the stock solution with additional water and additional acid;
    adding additional alcohol;
    adding a surfactant to form a sol-gel solution;
    depositing the sol-gel solution on a substrate;
    spinning the substrate; and
    heating the substrate.

21. The method of claim 20 wherein the surfactant is cetyltrimethylammonium bromide, the acid is hydrochloric acid and the alcohol is ethanol.

22. The method of claim 21 wherein the final molar ratio is tetraethylorthosilicate=about 1.0, water=about 0.0 to about 40.0, ethanol=about 0.0 to about 40.0 and hydrochloric acid=about 0.0001 to about 0.1.

23. The method of claim 20 wherein the weight percent of the surfactant is from 1 weight percent to 5 weight percent.

24. The method of claim 20 wherein the amount of surfactant is varied to vary the pore size in the permeation layer.

* * * * *